US011083575B2

(12) United States Patent
Gao et al.

(10) Patent No.: US 11,083,575 B2
(45) Date of Patent: Aug. 10, 2021

(54) HEART VALVE FRAME DESIGN WITH NON-UNIFORM STRUTS

(71) Applicant: Edwards Lifesciences Corporation, Irvine, CA (US)

(72) Inventors: Yong Gao, Irvine, CA (US); Pu Zhou, Dove Canyon, CA (US); Tianwen Zhao, Irvine, CA (US); Jeffrey Wu, Tustin, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 170 days.

(21) Appl. No.: 16/101,175

(22) Filed: Aug. 10, 2018

(65) Prior Publication Data

US 2019/0046315 A1    Feb. 14, 2019

Related U.S. Application Data

(60) Provisional application No. 62/545,343, filed on Aug. 14, 2017.

(51) Int. Cl.
*A61F 2/02* (2006.01)
*A61F 2/24* (2006.01)

(52) U.S. Cl.
CPC .......... *A61F 2/2418* (2013.01); *A61F 2/2433* (2013.01); *A61F 2220/0075* (2013.01);
(Continued)

(58) Field of Classification Search
CPC .................. A61F 2/2418; A61F 2/2433; A61F 2220/0075; A61F 2230/0006;
(Continued)

(56) References Cited

U.S. PATENT DOCUMENTS 3,409,013 A    11/1968 Berry
3,548,417 A    12/1970 Kisher
(Continued)

FOREIGN PATENT DOCUMENTS

DE    2246526 A1    3/1973
DE    0144167 C    6/1985
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Erich G Herbermann
(74) *Attorney, Agent, or Firm* — Calfee, Halter & Griswold LLP; Joel B. German

(57) ABSTRACT

An implantable prosthetic valve assembly, according to one embodiment, comprises a frame assembly including a plurality of struts and a prosthetic valve secured inside the frame assembly by sutures. The sutures are inward of the outermost surface of an outer periphery of the frame assembly. In certain embodiments the struts contain recesses in which sutures can be disposed. In other embodiments, the struts can have holes through them which the sutures pass through. The implantable prosthetic valve assembly can also be collapsed within a catheter such that an outermost surface of a periphery of the frame assembly touches the catheter but the sutures are spaced apart from the catheter or are flush with the outer surface of the frame.

21 Claims, 14 Drawing Sheets

(52) U.S. Cl.
CPC .............. *A61F 2230/0006* (2013.01); *A61F 2230/0008* (2013.01); *A61F 2230/0015* (2013.01); *A61F 2230/0019* (2013.01); *A61F 2230/0034* (2013.01); *A61F 2230/0054* (2013.01); *A61F 2230/0091* (2013.01)

(58) Field of Classification Search
CPC ...... A61F 2230/0008; A61F 2230/0015; A61F 2230/0019; A61F 2230/0034; A61F 2230/0054; A61F 2230/0091; A61F 2/24; A61F 2/2409; A61F 2/2412; A61F 2/2427; A61F 2/243; A61F 2/2436; A61F 2/2439; A61F 2/2454; A61F 2/246; A61F 2/2469

See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown |
| 6,783,542 B2 | 8/2004 | Eidenschink |
| 6,830,584 B1 | 12/2004 | Seguin |
| 6,878,162 B2 | 4/2005 | Bales et al. |

(56) References Cited

U.S. PATENT DOCUMENTS

| | | | |
|---|---|---|---|
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0073155 A1* | 4/2004 | Laufer ............... A61B 18/1477 |
| | | | 604/8 |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0295363 A1* | 12/2011 | Girard ................... A61F 2/2412 |
| | | | 623/1.26 |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0191178 A1* | 7/2012 | Laduca ................... A61F 2/07 |
| | | | 623/1.16 |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1* | 9/2014 | Garde .................. A61F 2/2403 |
| | | | 623/2.18 |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |

(56) References Cited

U.S. PATENT DOCUMENTS

| | | | |
|---|---|---|---|
| 2017/0014229 | A1 | 1/2017 | Nguyen-Thien-Nhon et al. |
| 2017/0042673 | A1 | 2/2017 | Vietmeier |
| 2018/0028310 | A1 | 2/2018 | Gurovich et al. |
| 2018/0153689 | A1 | 6/2018 | Maimon et al. |
| 2018/0325665 | A1 | 11/2018 | Gurovich et al. |
| 2018/0344456 | A1 | 12/2018 | Barash et al. |

FOREIGN PATENT DOCUMENTS

| | | | |
|---|---|---|---|
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | A1 | 3/1984 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| EP | 1579824 | A2 | 9/2005 |
| EP | 3181096 | A1 | 6/2017 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 9117720 | A1 | 11/1991 |
| WO | 9217118 | A1 | 10/1992 |
| WO | 9301768 | A1 | 2/1993 |
| WO | 9724080 | A1 | 7/1997 |
| WO | 9829057 | A1 | 7/1998 |
| WO | 9930646 | A1 | 6/1999 |
| WO | 9933414 | A1 | 7/1999 |
| WO | 0018333 | A1 | 4/2000 |
| WO | 0041652 | A1 | 7/2000 |
| WO | 0135878 | A2 | 5/2001 |
| WO | 0149213 | A2 | 7/2001 |
| WO | 0154624 | A1 | 8/2001 |
| WO | 0154625 | A1 | 8/2001 |
| WO | 0162189 | A1 | 8/2001 |
| WO | 0047139 | A9 | 9/2001 |
| WO | 0164137 | A1 | 9/2001 |
| WO | 0176510 | A2 | 10/2001 |
| WO | 0222054 | A1 | 3/2002 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 0249540 | A2 | 6/2002 |
| WO | 03047468 | A1 | 6/2003 |
| WO | 2005034812 | | 4/2005 |
| WO | 2005055883 | A1 | 6/2005 |
| WO | 2005084595 | A1 | 9/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2005102015 | A3 | 4/2007 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008094504 | A1 | 8/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009116041 | | 9/2009 |
| WO | 2009149462 | A2 | 12/2009 |
| WO | 2010011699 | A2 | 1/2010 |
| WO | 2010121076 | A2 | 10/2010 |
| WO | 2011104269 | A1 | 9/2011 |
| WO | 2013106585 | A1 | 7/2013 |
| WO | 2015085218 | A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

* cited by examiner

HEART VALVE FRAME DESIGN WITH NON-UNIFORM STRUTS

FIELD

The present disclosure relates to implantable devices and, more particularly, to valve prosthetics for implantation into the circulatory system, such as native heart valve annuluses.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques can be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. Another less drastic method for treating defective valves is through repair or reconstruction, which is typically used on minimally calcified valves.

When a valve is replaced, surgical implantation of a prosthetic valve typically requires an open-chest surgery during which the heart is stopped and patient placed on cardiopulmonary bypass (a "heart-lung machine"). In one common surgical procedure, the diseased native valve leaflets are excised and a prosthetic valve is sutured to the surrounding tissue at the valve annulus. By some estimates, more than 50% of the subjects suffering from aortic stenosis who are more than 80 years old cannot be operated on for aortic valve replacement.

Because of the drawbacks associated with conventional open-heart surgery, percutaneous and minimally-invasive surgical approaches are garnering intense attention. In one transvascular technique, a prosthetic valve is configured to be implanted in a much less invasive procedure by way of catheterization. For instance, U.S. Pat. Nos. 7,993,394, 5,411,522, 6,730,118, and 9,393,110, which are incorporated herein by reference, describe collapsible transcatheter heart valves that can be percutaneously introduced in a compressed state from a catheter and expanded at the desired position by balloon inflation or by utilization of a self-expanding frame or stent.

An important design parameter of a transcatheter heart valve is the diameter of the compressed, folded, or crimped profile. The diameter of the crimped profile is important because it directly influences the physician's ability to advance the valve through the femoral artery or vein. More particularly, a smaller profile allows for treatment of a wider population of patients.

Some transcatheter heart valve assemblies include a prosthetic valve secured to a collapsible stent or frame assembly by sewing or stitching the soft components to the stent or frame. Suture material is most often used, but any suitable means for attaching the prosthetic valve to the collapsible stent or frame assembly can be used. U.S. Pat. Nos. 7,993, 394 and 9,393,110 describe embodiments of transcatheter heart valve assemblies in which prosthetic heart valves are secured to a plurality of axial (i.e. vertical) and angled, circumferential struts and/or nodes by sutures that loop around the struts and/or nodes and through the prosthetic valve.

SUMMARY

An implantable prosthetic cardiac valve assembly including non-uniform struts and/or nodes is disclosed.

In certain disclosed embodiments, the prosthetic cardiac valve assembly comprises a collapsible and expandable frame or stent and a prosthetic valve secured within the collapsible and expandable frame or stent. The collapsible and expandable frame or stent can be formed of non-uniform struts. In certain embodiments, the collapsible and expandable frame or stent is formed of non-uniform struts and commissure attachment windows that attach to commissures of the prosthetic valve. In certain embodiments, the collapsible and expandable frame or stent is formed of non-uniform struts and attachment posts that attach to commissures of the prosthetic valve. In certain embodiments, the collapsible and expandable frame or stent assembly is formed of nitinol or preferably a nickel-cobalt alloy.

In some embodiments, the prosthetic heart valve has valve components of a Sapien 3 valve, made by Edwards Lifesciences. The disclosed invention can be used with this type or any other suitable type of valve.

In certain embodiments, the valve has a plurality of non-uniform struts that extend from a first end of the valve assembly to a second end. Some of the struts can extend straight from the first end (i.e. axially) and some of the struts can be angled or extend perpendicular to the axial direction. The struts can be multiple pieces or can be formed as one integral piece. The struts can have a rectangular cross-section, a rounded cross-section, a regularly shaped cross-section, an irregularly shaped cross-section, or a cross-section that changes shape along the length of the strut. The struts can be formed of braided or crimped wires. The struts can meet at junctions called nodes.

The plurality of non-uniform struts and/or nodes can have depressions of the same or different shapes along their length. Sutures disposed in these depressions are inward of an outermost surface of the prosthetic cardiac valve frame formed by the non-uniform struts. As such, the recessed sutures do not touch the inner surface of a catheter when the prosthetic cardiac valve assembly is collapsed within the catheter. Or, the sutures can be flush with the outermost surface of the prosthetic valve frame.

The plurality of non-uniform struts and/or nodes can have passages along their length. Sutures disposed through these passages are inward of an outermost surface of a periphery of the prosthetic cardiac frame such that sutures do not touch the inner surface of a catheter.

In certain embodiments, areas between holes in optional attachment posts are recessed such that sutures disposed through these holes are inward of an outermost surface of the prosthetic cardiac valve frame.

These features and others of the described embodiments will be more readily apparent from the following detailed description, which proceeds with reference to the accompanying figures.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but can optionally contain C or other components other than A and B. A device that includes or comprises A or B can contain A or B or A and B, and optionally one or more other components such as C.

Figure 1:
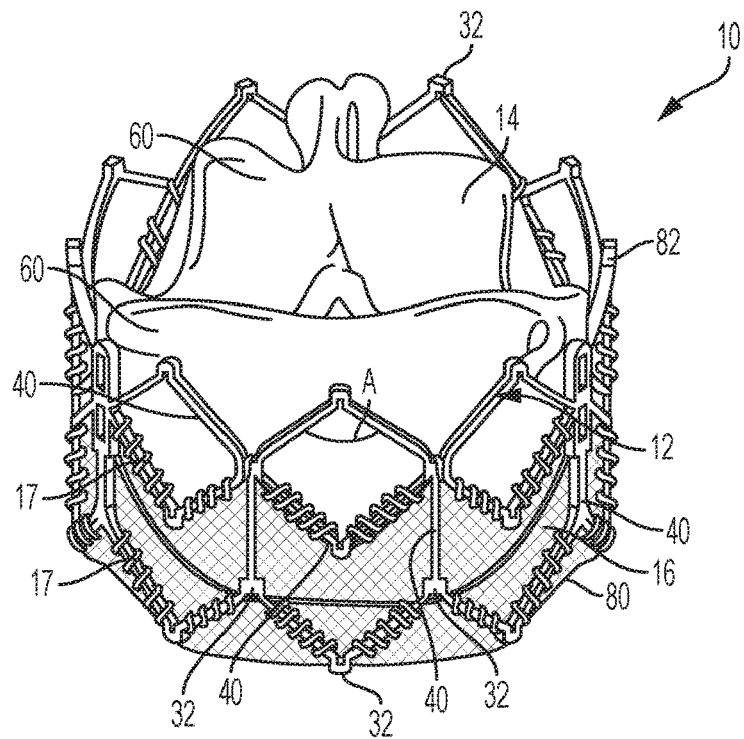
FIG. 1 is a perspective view of an embodiment of a prior art valve assembly.
Figure 2:
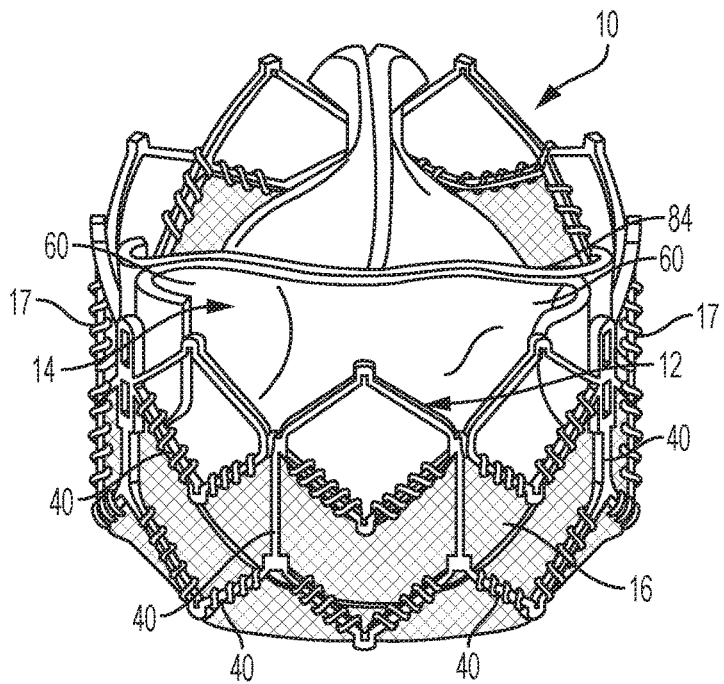
FIG. 2 is a perspective view of an embodiment of a prior art valve assembly.
Figure 2A:
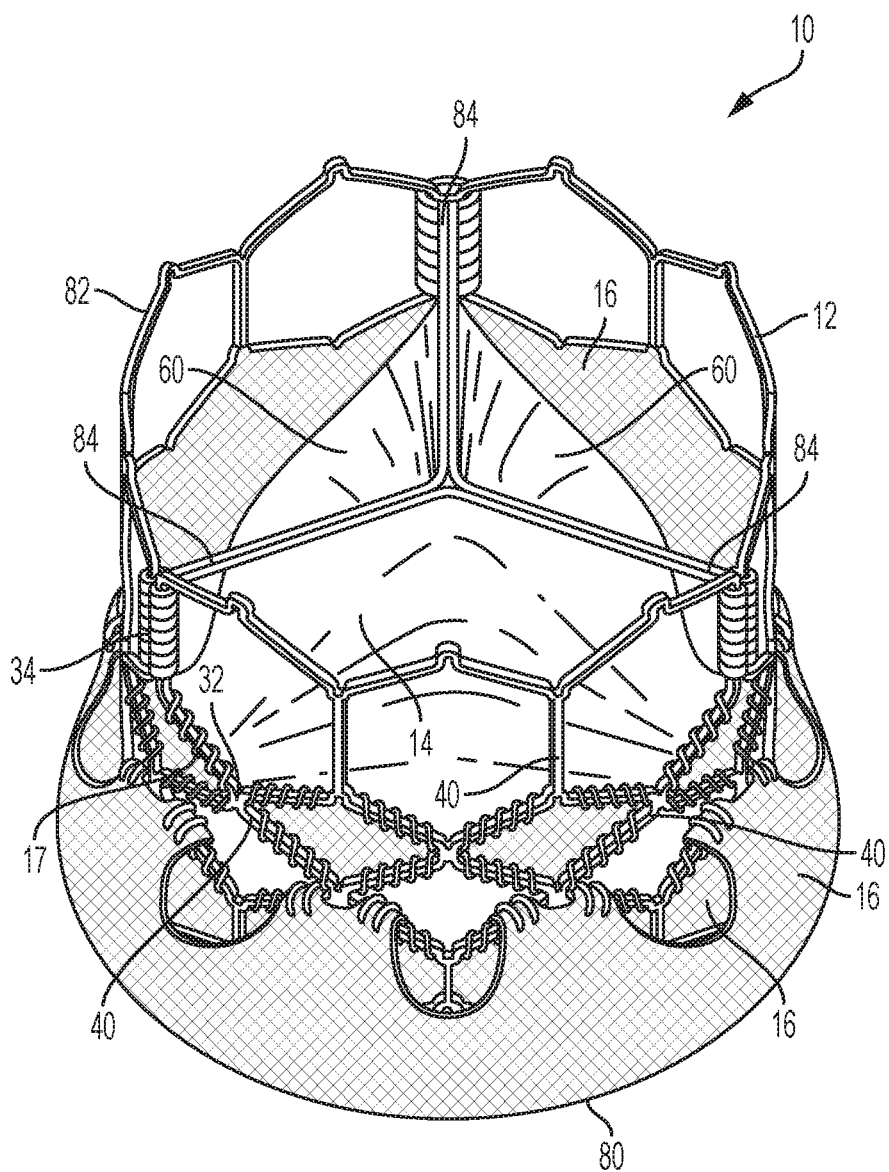
FIG. 2A is a perspective view of an embodiment of a prior art valve assembly.
Figure 4:
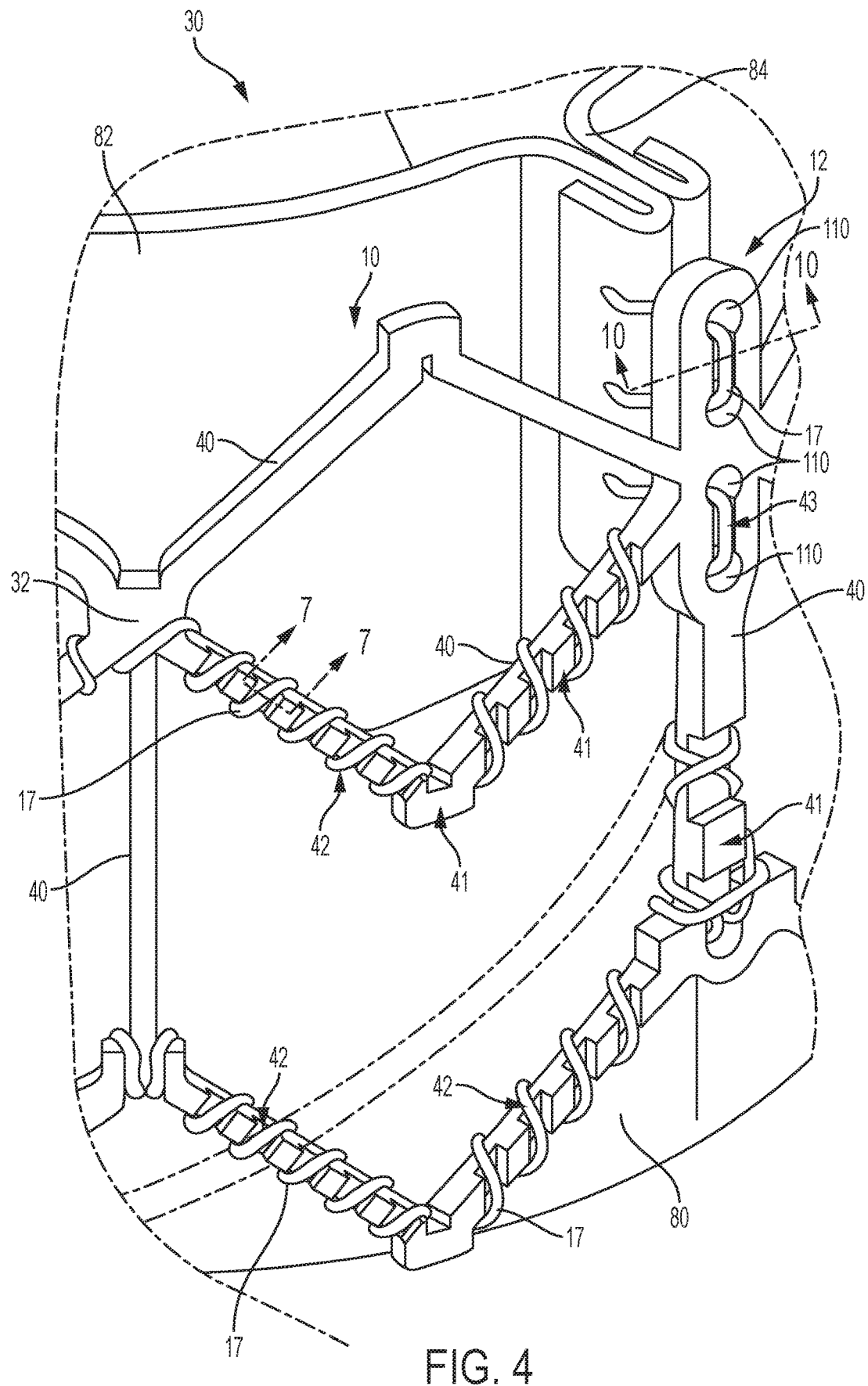
FIG. 4 is a magnified, cut-away view of an embodiment of a heart valve assembly having non-uniform struts with recesses.

Referring to FIGS. 1, 2A, and 4, the present application relates to implantable prosthetic devices 10 with frames 12 that are configured to inwardly offset sutures 17 used to attach valve components to the frame 12. The term "suture," as used in this application, includes, but is not limited to, polymer materials (e.g., Ethibond sutures), thread, strand, fiber, wire, other windable materials, organic and inorganic materials, or any other material that is acceptable for medical applications and is suitable for joining together the materials used in the various embodiments of the valve assembly.

The frame 12 can take a wide variety of different forms. While the present application primarily illustrates heart valves as examples, the frame 12 can be the frame of a stent, a docking station, etc. The sutures 17 can attach a wide variety of different structures to the frame 12. For example, the sutures 17 can attach valve components, covering material, valves, etc. to the frame 12. As shown in FIG. 4, the inward offsetting of the sutures 17 minimizes contact or interaction between the sutures and the valve delivery and/or recapture system and can slightly decrease the overall profile of a crimped valve. In one exemplary embodiment, an outermost surface of the suture can be flush or substantially flush with an outermost surface of the valve frame. Suture damage or breakage due to abrasion or fraying is reduced, and the possibility of damage to the delivery or recapture system (including to the tip of an expandable sheath or tip of a delivery cylinder) from the sutures is also reduced. The pushing force or resistance on the valve as it is passed through the delivery or recapture system is also reduced by minimizing the suture exposure on the outer diameter of the frame, and by minimizing the interaction between the sutures and the delivery or recapture system. This also results in lower maximum stress or strain on a valve assembly during crimping or expansion in delivery, recapture, and fully deployed conditions.

The concepts described in this application can be used with a wide variety of different valve assemblies. Two of the many valve assemblies that can use the concepts disclosed by the present application are disclosed by U.S. Pat. No. 7,993,394 (see FIGS. 1, 2, and 3) and U.S. Pat. No. 9,393,110 (see FIGS. 2A and 3A). Referring to FIGS. 1, 2, and 2A, the prosthetic valve 10 disclosed by U.S. Pat. Nos. 7,993,394 and 9,393,110 each comprise a frame, or stent, 12, a leaflet structure 14 supported by the frame, and skirt 16. The valves 10 are typically implanted in the annulus of the native aortic valve but also can be adapted to be implanted in other native valves of the heart or in various other ducts or orifices of the body.

Each of the valves 10 has a "first" end 80 and a "second" end 82. In the context of the present application, the terms "first" and "second" are used interchangeably with the terms "inflow" and "outflow", respectively. Thus, for example, in the embodiments illustrated in FIGS. 1, 2, and 2A, the first end 80 of the valve is its inflow end and the second end 82 of the valve is its outflow end.

The valves 10 are configured to be radially collapsible to a collapsed or crimped state for introduction into the body on a delivery catheter and radially expandable to an expanded state for implanting the valve at a desired location in the body (e.g., the native aortic valve). The frames 12 can be made of an expandable material that permits crimping of the valve to a smaller profile for delivery and expansion of the valve using an expansion device such as a balloon. Mechanically expandable frames are also contemplated. Exemplary plastically-expandable materials that can be used to form the frame are described below.

Alternatively, valves 10 can be a so-called self-expanding valve wherein the frame is made of a self-expanding material such as Nitinol. A self-expanding valve can be crimped to a smaller profile and held in the crimped state with a restraining device such as a sheath covering the valve. When the valve is positioned at or near the target site, the restraining device is removed to allow the valve to self-expand to its expanded, functional size.

In the examples of FIGS. 1, 2, 2A and 3A, the frame 12 is an annular, stent-like structure comprising a plurality of vertical and angled struts 40. In this application, the term strut encompasses vertical struts, angled struts, attachment posts, commissure windows, and any similar structures described by U.S. Pat. Nos. 7,993,394 and 9,393,110. A strut may be any elongated member or portion of the frame 12. In the illustrated examples, the struts are connected together at nodes or connecting portions 32. The frames 12 can have one or more multiple rows that can be made up of angled and vertical struts Additional details of the frames 12 illustrated by FIGS. 1, 2, 2A, and 3A can be found in U.S. Pat. Nos. 7,993,394 and 9,393,110.

Prosthetic valves 10 can have leafed-valve configurations. The valves 10 can be formed from pieces of flexible, pliant material connected to each other at seams (also referred to as commissure tabs) to form collapsible prosthetic valve leaflets 60. The valves 10 can be connected to their respective frames, 12, at the seams using, for example, sutures 17 and/or flexible connectors 34 (see FIG. 2A). Alternatively, the valves 10 can be a mechanical type valve, rather than a leafed type valve.

The valves 10 can be made from biological matter, such as natural tissue, pericardial tissue (e.g., bovine, porcine or equine pericardium), a harvested natural valve, or other biological tissue. Alternatively, the valves 10 can be made from biocompatible, synthetic materials (e.g., biocompatible polymers), which are well known in the art. The valves 10 can be shaped to fit the contours of the frames 12 so as to match the frame assemblies in diameter. Flow through the valves 10 proceeds in a direction from first end 80 to second end 82.

Figure 3:
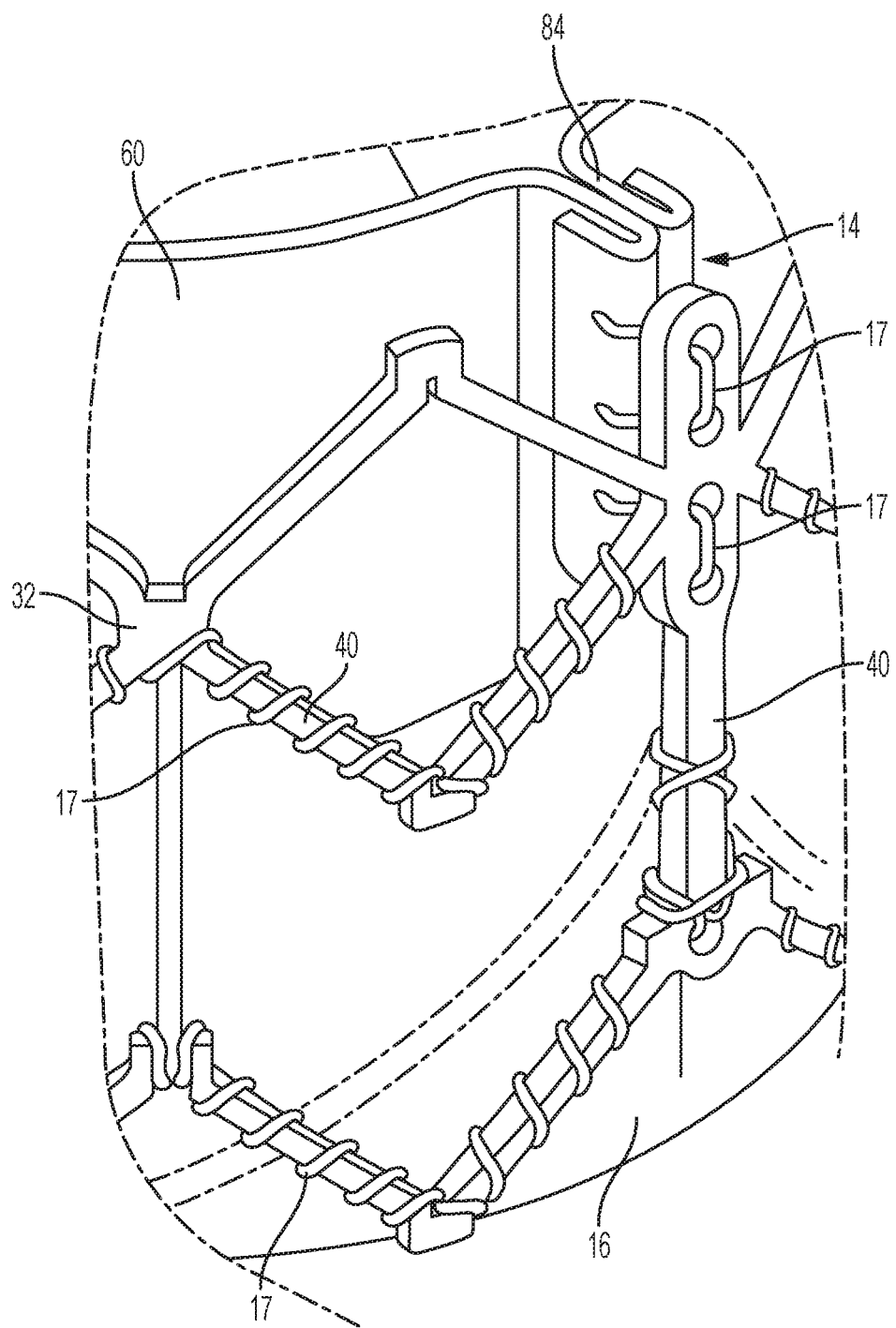
FIG. 3 is a magnified, cut-away view of the prior art valve assembly illustrated by FIG. 1.
Figure 3A:
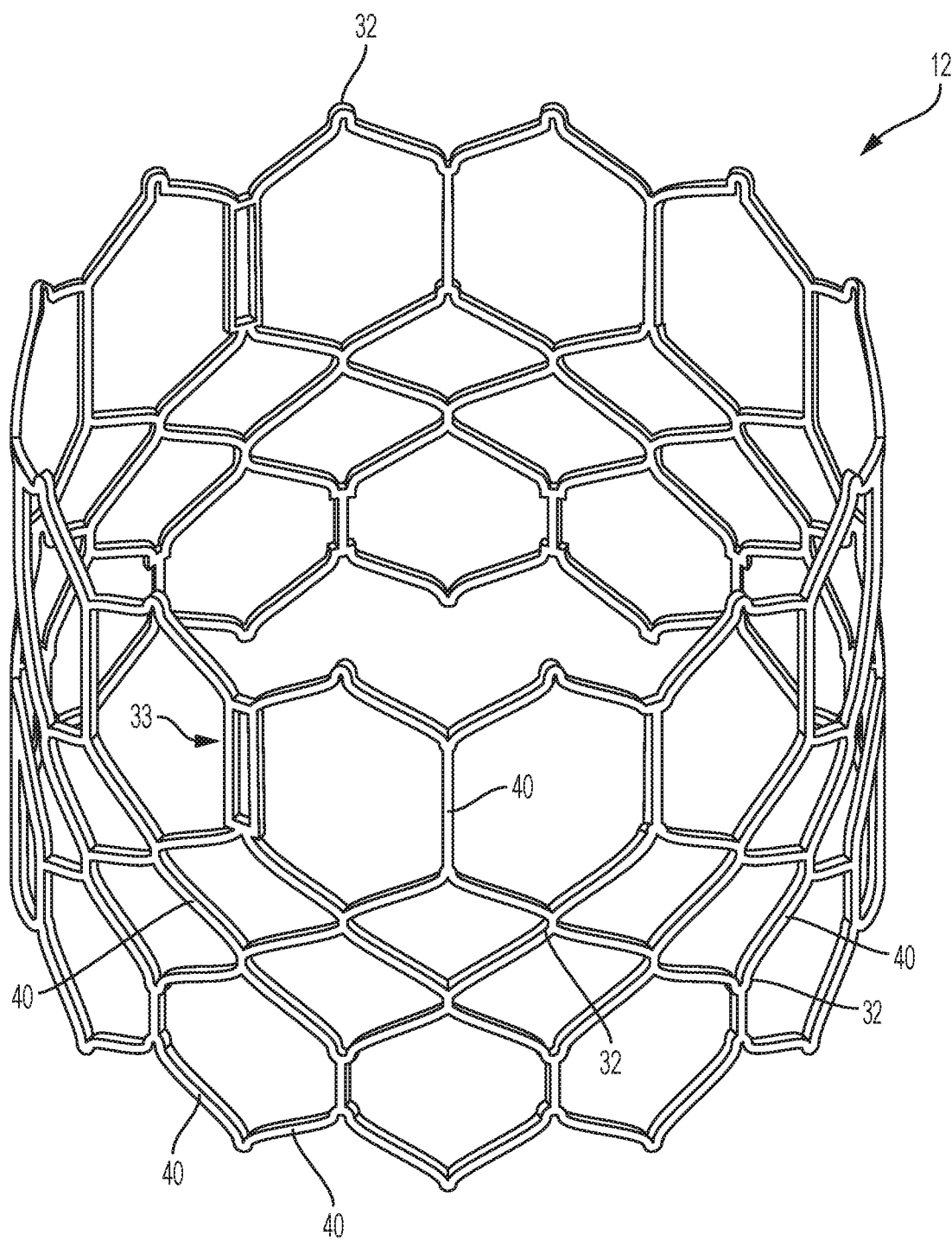
FIG. 3A is an embodiment of a prior art valve.

Leaflets 60 can be secured to one another at their adjacent sides to form commissures 84 of the leaflet structure (the edges where the leaflets come together). For example, as shown in FIG. 3, commissures 84 of the leaflet structure 14 can be secured to struts 40 using sutures. Sutures 17 can also be used to attach skirt material 16 to the frame. In another example, as shown in FIG. 2A, commissures 84 of the leaflet structure 14 can be aligned with commissure window portion 33 (of FIG. 3A) or other attachment areas in the frame and secured thereto using flexible connectors 34 (shown in FIG. 2A).

FIG. 3 further illustrates an implantable prosthetic valve 10 in a magnified, cut-away view wherein the skirt 16 has been removed, but the sutures 17 used to attach the skirt material 16 and the leaflets 60 to the frame 12 remain. FIG. 3 also illustrates how sutures 17 can be wrapped around the struts 40 of frame assembly 12. Sutures 17 can pass through portions of leaflet assembly 14 and/or skirt 16 to secure them to the frame. Sutures 17 secure commissures 84 to vertical struts by looping through spaced apart attachment holes.

Additional details of the construction of the valves shown in FIGS. 1, 2, and 2A can be found in U.S. Pat. Nos. 7,993,394 and 9,393,110.

Suitable materials that can be used to form a frame include, without limitation, stainless steel, nickel based alloy (e.g., a nickel-cobalt-chromium alloy), and polymers, or combinations thereof. In particular embodiments, frames 12 can be made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum by weight.

Referring again to FIGS. 1, 2, and 2A, the inner skirt 16 can comprise a tough, tear resistant material such as PET, although various other synthetic or natural materials can be used. The main functions of the inner skirt 16 are to assist in securing the leaflet structure 14 to the frame 12 and to assist in forming a good seal between the valve and the native annulus by blocking the flow of blood through the open cells of the frame 12 below the lower edge of the leaflets.

Referring now to FIG. 4, in one exemplary embodiment non-uniform struts 40 allow attachment sutures 17 to secure a prosthetic cardiac valve 12 and/or skirt 16 to a collapsible and expandable frame or stent such that the sutures 17 are recessed away from the inner surface or inner diameter of a catheter when the prosthetic valve assembly is collapsed and inserted into a catheter for delivery to the site of implantation. Or, the sutures 17 can be flush with an outer surface of the frame 12. The prosthetic cardiac valve assembly can incorporate different valve and frame structures than those described above in FIGS. 1, 2, 2A, 3 and 3A in addition to the inventive features described below. In some embodiments, the inventive concepts can be applied to a Sapien 3 valve, made by Edwards Lifesciences. The disclosed invention can be used with any other catheter implanted device, including any other valve, stent, docking station, or frame-like structure.

FIG. 4 illustrates one embodiment of a prosthetic cardiac valve assembly 30 that has a plurality of axially extending and angled struts 40 and nodes 32. The struts 40 extend from first end 80 to second end 82 and form a periphery of the prosthetic cardiac valve assembly 30. The illustrated periphery is cylindrical in shape, but other shapes can be formed. For example, the periphery of the frame can be oval shaped, kidney shaped, or shaped to approximate the shape of a valve annulus, such as the mitral valve annulus, the pulmonary valve annulus, or the tricuspid valve annulus. The periphery formed by the struts 40 has a radially outermost surface 41 and a plurality of recesses 42 and/or recesses 43. In this application, the radial direction is perpendicular to a direction of travel from the first end 80 to the second end 82. An object that is "radially inward" is closer to the center of the valve than an object that is "radially outward." In FIG. 4, recesses 42 and 43 are radially inward of the outermost surface of the periphery 41 such that sutures 17 can secure valve 10 to frame assembly 12 without extending radially beyond the outermost surface of the periphery 41. In one exemplary embodiment, when prosthetic valve assembly 30 is collapsed and inserted in a catheter for delivery, sutures 17 do not touch the inner surface of the catheter. In another exemplary embodiment, the sutures are flush with the outermost surface of the periphery 41.

Recesses in struts also allow for faster and more accurate placement of securing sutures 17 in either manual or automated production/assembly (e.g., easier to count the appropriate number of sutures, space sutures along a frame strut, or appropriately control suture tension). Additionally, sutures 17 in recesses are less likely to change position relative to the frame assembly either in in the frame assembly because attrition and frictional forces are minimized (with recessed struts, frictional forces are not the only force securing the sutures in place and accordingly need not be as high in magnitude).

In certain embodiments, the cross-sections of struts 40, described above with reference to FIG. 4, are not rectangular, but rounded, circular, having a polygonal shape, having an irregular shape, or having a shape that changes along the length of the strut. The cross-sections of the struts can also remain the same shape, but change size along the length of the strut or going from the first end 80 to the second end 82 of the prosthetic cardiac valve assembly.

Additionally, while recesses 42 in FIG. 4 are shown evenly spaced, recesses in other embodiments can be irregularly spaced or spaced differently for different struts. Struts 40 and nodes 32 can be made thicker in non-recessed cross-section to accommodate recesses. Recesses can generally be placed in thicker struts or nodes to ensure structural integrity of the strut or node.

Figure 6:
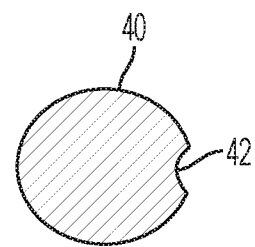
FIG. 6 is a cross-sectional view taken along the plane indicated by lines 6-6 in FIG. 5.
Figure 7:
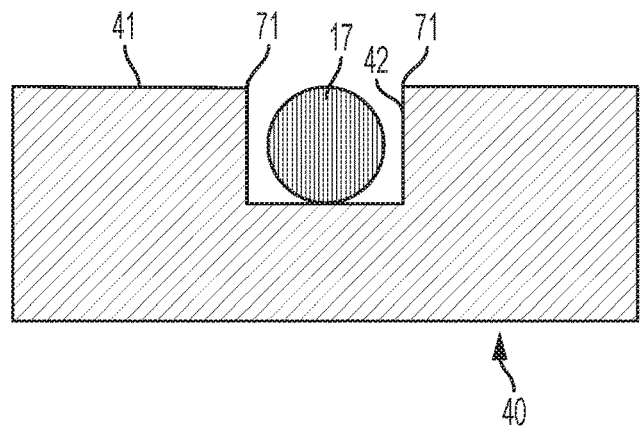
FIG. 7 is a cross-sectional view taken along the plane indicated by line 7-7 of FIG. 4.

Referring to FIG. 7, a cross-section of a recess 42 taken along line 7-7 in FIG. 4 shows a rectangular recess with square corners 71 (FIG. 7). In other embodiments recesses can be rounded, semi-circular, angular, polygonal, irregular in shape, or have a changing cross-section, and can have a variety of corner shapes. Examples of embodiments with recesses having different cross-sections are described below with reference to FIGS. 6-9.

Recesses 42 are depressions in the radially outermost surface of the periphery 41 of strut 40 as seen in FIG. 4. In still further embodiments, recesses can be depressions in any surface of a non-uniform strut. Such recesses can form a helical and continuous depression along the strut's surface, depressions in a radially inward surface of a strut, multiple depressions on multiple sides of a strut, continuous depressions around the circumference or perimeter of a strut, or other configurations.

Figure 5:
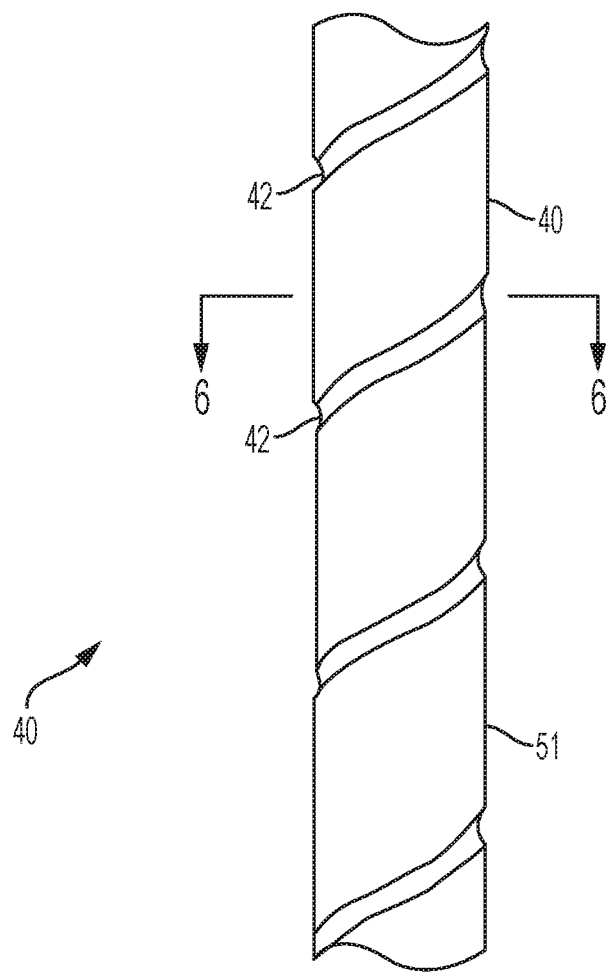
FIG. 5 is a side view of an embodiment of a non-uniform strut with a rounded, continuous, helical recess.

FIGS. 5 and 6 show an embodiment of a strut 40 with a circular cross-section and a recess 42 that is helical. For example, the strut illustrated by FIG. 5 has a non-recessed portion 51. In this embodiment, the outermost surface of the valve periphery is a line along the non-recessed portion of the strut 40 that is furthest from the center of the cardiac valve assembly. The recess 42 with a helical path is radially inward of non-recessed portion 51, such that a securing suture 17 in recess 40 would be radially inward of non-recessed portion 51. A suture 17 in the recess 42 with a helical shape is radially inward of the outermost surface of the periphery of the valve assembly. While the helical embodiment is illustrated in FIGS. 5 and 6 as a regular, continuous helical recess, the helical recesses can be interrupted or irregular in shape and spacing.

FIG. 6 shows a cross-section of the non-uniform strut 40 taken along a plane indicated by lines 6-6. The illustrated recess 42 is a rounded recess with non-rounded corners. This recess in alternate embodiments could have differently shaped cross-sections with different corner configurations, such as rounded and/or chamfered corners.

Figure 8:
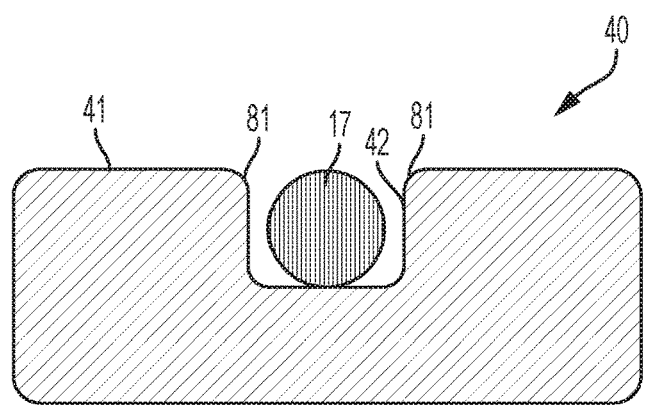
FIG. 8 is a cross-sectional view of an embodiment of a non-uniform strut that is similar to the embodiment illustrated by FIG. 7 where the strut has a recess that is rounded.
Figure 9:
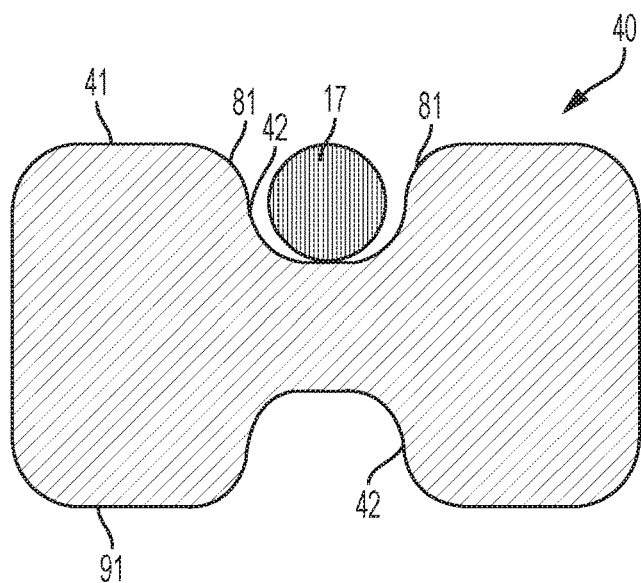
FIG. 9 is a cross-sectional view of an embodiment of a non-uniform strut that is similar to the embodiment illustrated by FIG. 7 where the non-uniform strut has inner and outer recesses.

FIG. 8 is a cross-sectional view that is similar to the view of FIG. 7. FIG. 8 illustrates that the strut 40 can have a recess that is rounded, with rounded corners. The recess is in an outermost surface of a periphery 41 of the frame 12. FIG. 9 is a cross-sectional view that is similar to the view of FIG. 7. FIG. 9 illustrates that the strut 40 can have recesses at both the inner surface 91 and the outer surface 41 such as any of the shaped illustrated by FIGS. 7-9. In the FIG. 9 embodiment, the strut has recesses 42 that are rounded with rounded corners 81. The recess 42 can extend around the circumference of the strut or two discrete recesses can be formed on opposite sides of the strut. Surface 91 is the radially innermost surface of the strut.

Figure 10:
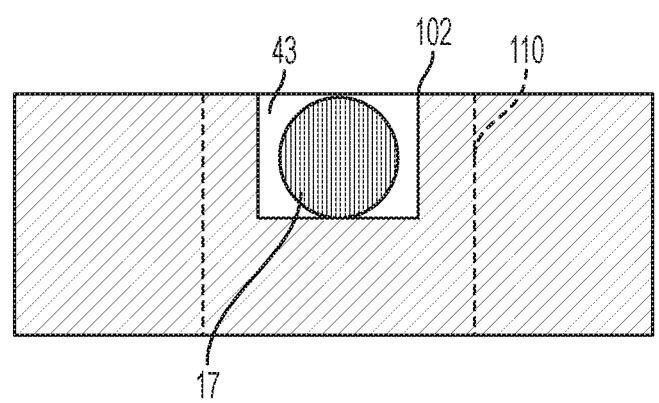
FIG. 10 is a cross-sectional view taken along the plane indicated by line 10-10 of FIG. 4.

FIG. 10 is a cross-sectional view of an embodiment of a strut 40 that is vertical and a suture 17 taken along the plane indicated by line 10-10 in FIG. 4. In the example illustrated by FIGS. 4 and 10, the recess 43 extends between two holes 110 that the suture 17 passes through. The recess 43 is illustrated as rectangular with square corners 102. However, the recess can have any shape. As shown in FIG. 10, recess 40 allows the suture 17, that extends between the holes and is disposed in recess 43, to be inward or flush with the radially outermost surface of the periphery 41. Thus suture 17 would not touch (or would touch with minimal force) the inner surface of a catheter.

Figure 11:
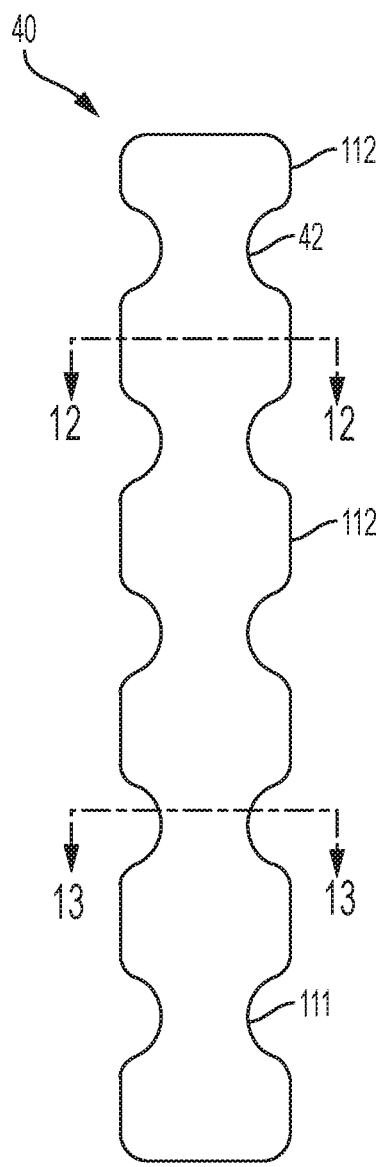
FIG. 11 is a side view of an embodiment of a non-uniform, circular cross-sectioned, strut with a plurality of recesses that each follow the circumference of the strut.
Figure 12:
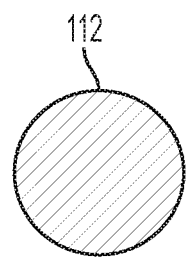
FIG. 12 is a cross-sectional view taken along the plane indicated by line 12-12.
Figure 13:
FIG. 13 is a cross-sectional view taken along the plane indicated by line 13-13.

FIGS. 11-13 show side and cross-sectional views of an embodiment of a strut 40 that is non-uniform, circular cross-sectioned, and integrally formed. The strut has a plurality of recesses 42 that each follow the circumference of the strut. Recesses following the circumference or perimeter of a strut can further ease placing of sutures 17. FIG. 12 is a cross-sectional view of a non-recessed portion 112 of strut 40 taken along the plane indicated by line 12-12 in FIG. 11. FIG. 13 is a cross-sectional view of a recessed portion 111 of the strut 40 taken along the plane indicated by line 13-13 in FIG. 11. The diameter of the cross-section of the non-recessed portion 112 is notably larger than the diameter of the cross-section of the recessed portion 111, such that a suture 17 in a recess 42 of strut 40 would be radially inward of or flush with the outermost surfaces of the non-recessed portions 112.

Struts as described herein can be formed of any of the materials described above as suitable for formation of the frame assembly (desirably a nickel-cobalt based alloy or a Nitinol material). In certain embodiments disclosed here, each strut is integrally formed of one piece. In other embodiments, struts can be formed of multiple pieces or can be formed of multiple wires, such as braided or otherwise bundled wires.

Figure 14:
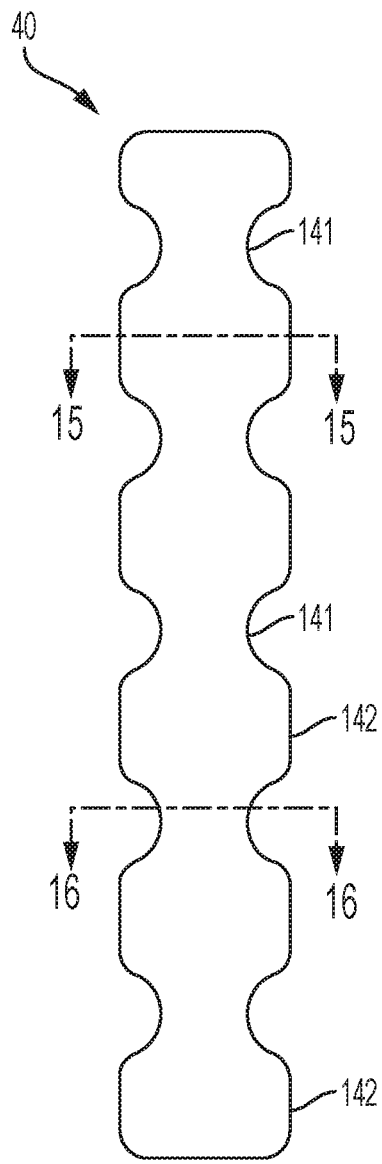
FIG. 14 is a side view of an embodiment of a non-uniform, circular cross-sectioned strut formed of braided wires, with a plurality of recesses that each follow the circumference of the strut.
Figure 15:
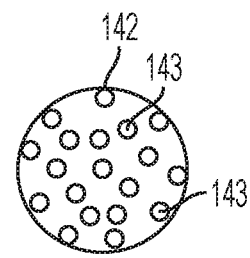
FIG. 15 is a cross-sectional view taken along the plane indicated by line 15-15 showing individual wires loosely packed.
Figure 16:
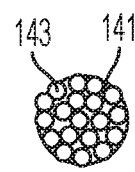
FIG. 16 is a cross-sectional view taken along the plane indicated by line 16-16 showing individual wires tightly packed.

FIGS. 14-16 are side and cross-sectional views of an embodiment of a strut 40 having a non-uniform, circular cross-section, said strut 40 formed of wires 143. The wires 143 may be braided or otherwise bundled. The struts 40 have a plurality of recesses 141 that each follow the circumference of the strut. FIG. 15 is a cross-sectional view of a non-recessed portion 142 of the strut 40 taken along the plane indicated by line 15-15 in FIG. 14. In FIG. 15, individual wires 143 are loosely packed to form a wider diameter. FIG. 16 is a cross-sectional view of a recessed portion 141 of the strut 40 taken along the plane indicated by line 16-16 in FIG. 14. In FIG. 16, individual wires 143 are more tightly packed to form a narrower diameter. The diameter of the cross-section of non-recessed portion 142 is notably larger than the diameter of the cross-section of recessed portion 141 such that a suture 17 in a recessed portion 141 of strut 40 would be radially inward of or at least flush with the outermost surfaces of the non-recessed portions 142.

Alternatively, an embodiment of a strut can be formed using braided wires, wherein the changing diameter of the wires forms the recessed and non-recessed portions of the strut instead of the relative tightness of packing/braiding. At portions of such a strut, wires would have wider diameters, naturally forming non-recessed portions of the strut, and at other portions of such a strut, the same wires would have narrower diameters, naturally forming recessed portions of the strut. In further embodiments, combinations of wire diameters and tightness of wire packing/braiding can be used to create recessed and non-recessed portions.

Figure 17:
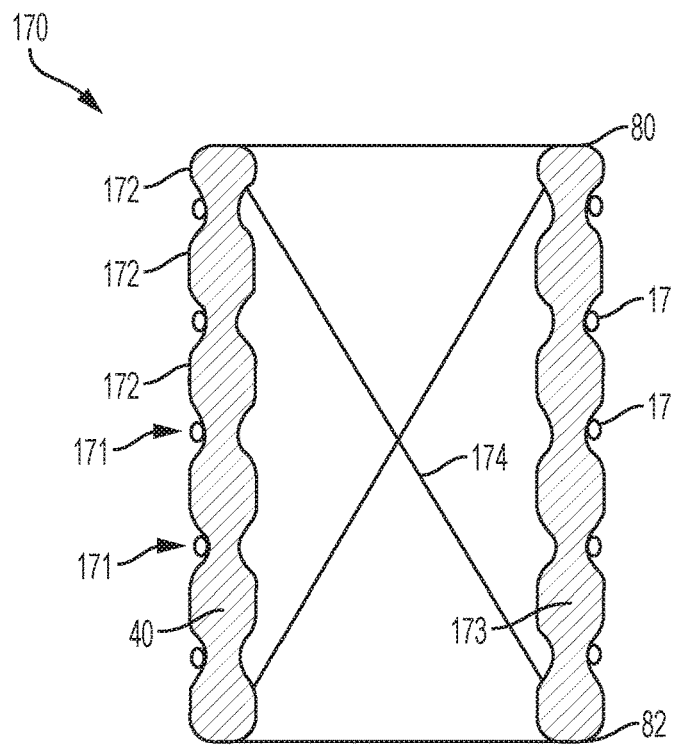
FIG. 17 is a cross-sectional view of an embodiment of an expanded cardiac valve assembly including a schematic representation of a valve and non-uniform struts.
Figure 18:
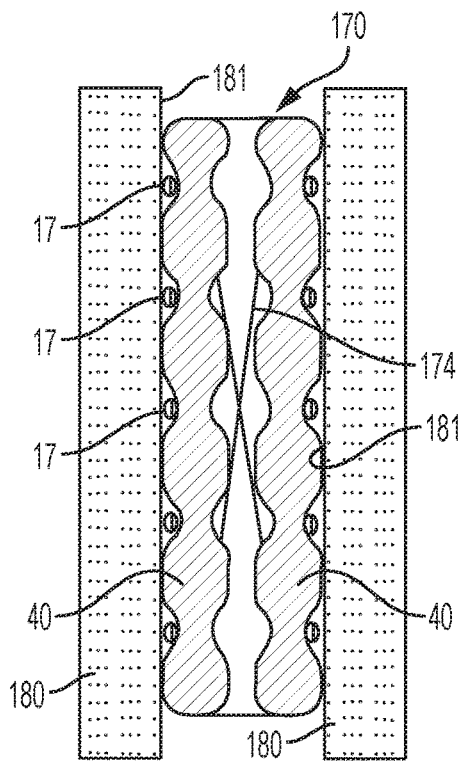
FIG. 18 is a cross-sectional view of the valve assembly of FIG. 17 collapsed in a catheter.

FIG. 17 is a schematic cross-sectional view of an embodiment of an expanded cardiac valve assembly 170. The valve assembly 170 includes a valve 174 (schematically illustrated), non-uniform struts 40 that form a frame assembly, and sutures 17. The struts have recessed portions 171 and non-recessed portions 172. Sutures 17 secure the valve 174 to struts 40. FIG. 18 illustrates the valve assembly 170 in collapsed form within a catheter 180. An inner surface 181 of the catheter 180 is flush with the outermost surface of the periphery formed by struts 40. Sutures 17 secure the valve 174 to the struts 40 without touching the inner surface 181 of catheter 180 as the sutures 17 are disposed in the recesses 42.

Figure 19:
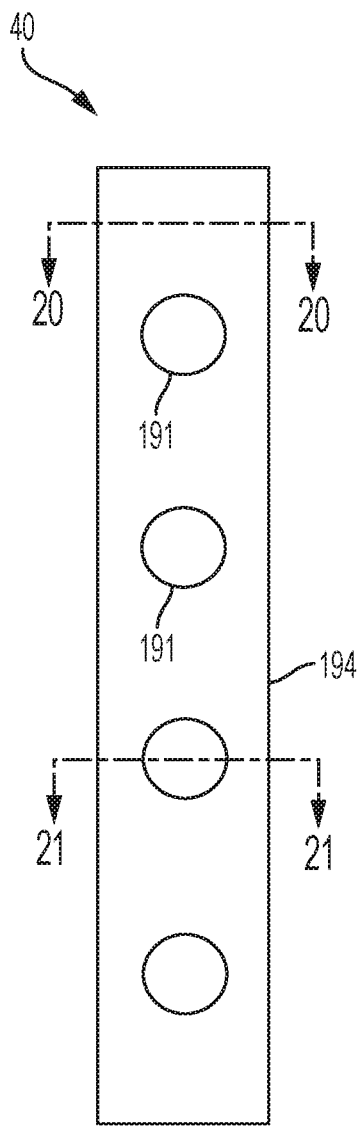
FIG. 19 is a side view of an embodiment of a circular cross-sectioned strut with a plurality of holes that pass through the non-uniform strut.
Figure 20:
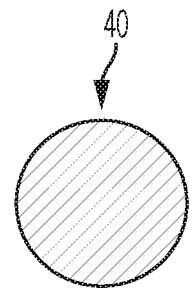
FIG. 20 is a cross-sectional view taken along the plane indicated by line 20-20 in FIG. 19.
Figure 21:
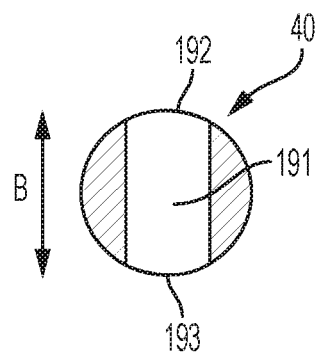
FIG. 21 is a cross-sectional view taken along the plane indicated by line 21-21 in FIG. 19.

In still further embodiments described herein, struts 40 (angled and axially extending) and nodes 32 making up a frame assembly can contain holes through which sutures 17 can pass to secure a valve or other structure to the frame assembly. FIG. 19 shows a side view of an embodiment of a strut 40 having a circular cross-section and a plurality of holes 191 that pass through the strut 40. Sutures 17 can pass through holes 191 to secure a valve to strut 40 such that sutures 17 are inward from radially outermost surface 194 of strut 40 (i.e. the axes of the holes are generally parallel to the outer surface of the frame formed from the struts 40, rather than being generally perpendicular to the outer surface of the frame). FIG. 20 is a cross-sectional view of a portion of the strut 40 without any holes, taken along the plane indicated by line 20-20 in FIG. 19. This cross-section is solid, without any empty space, but can be hollow or have another non-solid configuration. FIG. 21 is a cross-sectional view of a portion of the strut 40 with a hole, taken along the plane indicated by line 21-21 in FIG. 19. Arrow B indicates the circumferential direction in the plane of the cross-section in FIG. 21 (i.e. around the circumference of an overall cardiac valve assembly). Holes 191 pass directly through strut 40, entirely in the circumferential direction, from first hole opening 192 to second hole opening 193. As such, the sutures 17 are spaced apart from the outer circumference of the frame.

In alternative embodiments, struts can contain holes that do not strictly follow the circumferential direction. A hole can have a first hole opening that is substantially in line with the circumferential direction and then a second hole opening that is angularly displaced from the first, either to be more in line with the radial direction, or to be directed more at the first end 80 or second end 82 of the cardiac valve assembly, or a combination of the two. Holes can form angular or rounded turns mid-strut, or can form straight lines from a first hole opening to a second hole opening through a strut. In still further embodiments, holes are not spaced evenly along struts as they are with holes 191 in strut 40. In all embodiments of prosthetic cardiac valve assemblies including holes, holes are oriented such that sutures 17 disposed through the holes to secure a valve or skirt 16 to the struts 40 are inward of the radially outermost surface of the periphery of the frame formed by the struts.

Figure 22:
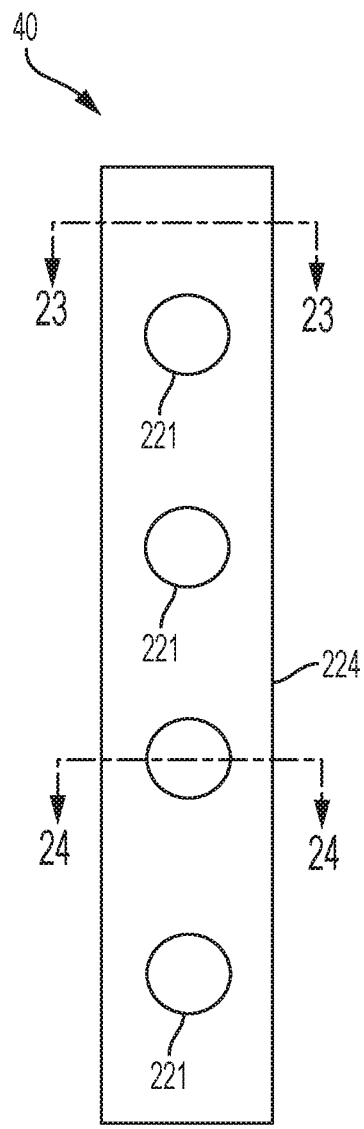
FIG. 22 is a side view of an embodiment of a hollow, circular cross-sectioned strut, with a plurality of holes that pass through the strut.
Figure 23:
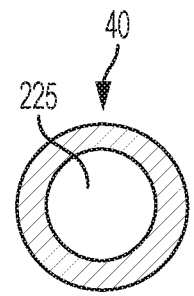
FIG. 23 is a cross-sectional view taken along the plane indicated by line 23-23 in FIG. 22.
Figure 24:
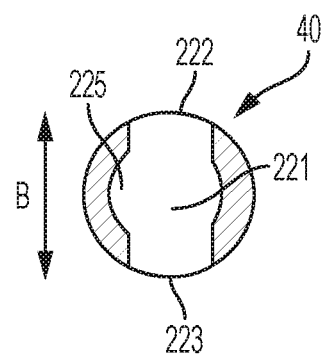
FIG. 24 is a cross-sectional view taken along the plane indicated by line 24-24 in FIG. 22.

In further embodiments of the present prosthetic cardiac valve, non-uniform struts and/or nodes making up a frame assembly can be hollow. Hollow, non-uniform struts can have recesses, holes, or both features. FIG. 22 shows a side view of an embodiment of a strut 40 having a hollow, circular cross-section with a plurality of holes 221 that pass through the strut 40. Sutures 17 can pass through the holes 221 to secure a valve and/or skirt 16 to strut 40 such that sutures 17 are inward from radially outermost surface 224 of strut 40 (i.e. the axes of the holes are generally parallel to the outer surface of the frame formed from the struts 40, rather than being generally perpendicular to the outer surface of the frame). FIG. 23 is a cross-sectional view of a portion of the hollow strut 40 taken along the plane indicated by line 23-23 where there are no holes. A passage 225 extends through the strut. FIG. 24 is a cross-sectional view of a portion of the strut 40 taken with a hole 221, along the plane indicated by line 24-24. Arrow B indicates the circumferential direction in the plane of the cross-section in FIG. 24 (with respect to an overall cardiac valve assembly). Holes 221 pass directly through strut 40, entirely in the circumferential direction, from first hole opening 222 to second hole opening 223. As such, the sutures are spaced apart from the outer circumference.

Figure 25:
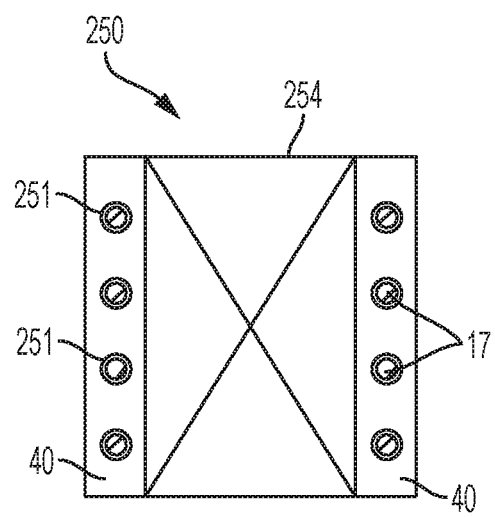
FIG. 25 is a cross-sectional view of an embodiment of an expanded cardiac valve assembly including a schematic representation of a valve and struts with holes.
Figure 26:
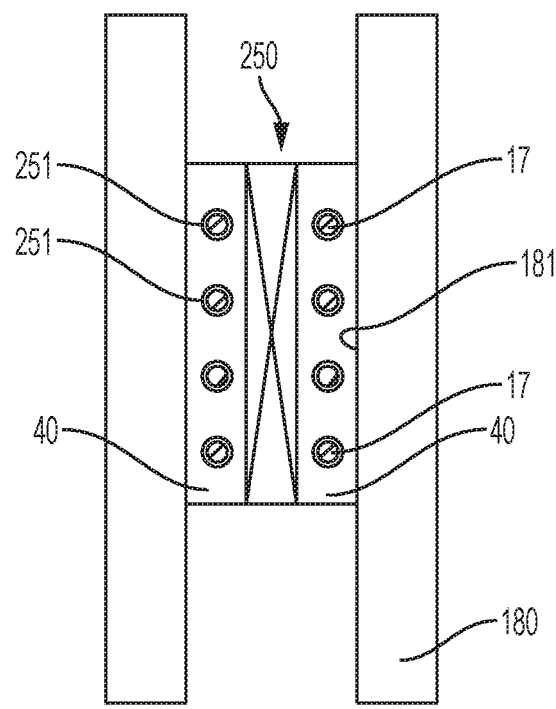
FIG. 26 is a cross-sectional view of the valve of FIG. 25 collapsed in a catheter.

FIG. 25 is a cross-sectional view of an embodiment of an expanded cardiac valve assembly 250 including a valve 254 that is schematically illustrated, struts 40 that form a frame, and sutures 17. The struts 40 have holes 251 that pass through the struts 40 in a generally circumferential direction. Sutures 17 secure the valve 254 to struts 40. FIG. 26 illustrates valve assembly 250 in a collapsed form within a catheter 180. An inner surface 181 of the catheter 180 is flush and in contact with the radially outermost surface of the periphery formed by struts 40. The sutures 17 secure the valve 254 to struts 40 without touching the inner surface 181 of the catheter 180, as sutures 17 are disposed through the holes 251.

Having illustrated and described the principles of the illustrated embodiments, it will be apparent that the embodiments can be modified in arrangement and detail without departing from such principles.

Further, although the prosthetic valve assemblies of this disclosure are shown generally circular in cross section, these prosthetic valve assemblies can have a D-shape, an oval shape, a kidney shape, the shape of any native heart valve, or any other shape suitable for fitting the contours of the relevant, replaced, native valve.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments, it will be recognized that the illustrated embodiments include only examples of the invention and should not be taken as a limitation on the scope of the invention. Rather, the invention is defined by the following claims. We therefore claim as the invention all such embodiments that come within the scope of these claims.

We claim:

1. An implantable prosthetic valve assembly comprising: a collapsible and expandable frame having a plurality of spaced struts that extend from a first end of the collapsible and expandable frame to a second end of the collapsible and expandable frame and define an outer periphery of the collapsible and expandable frame having an outermost surface; wherein the plurality of spaced struts include a plurality of recesses that extend radially inward from the outermost surface of the outer periphery; a prosthetic valve secured within the collapsible and expandable frame by sutures; wherein the sutures are disposed in the plurality of recesses, wherein the sutures secure the valve to the collapsible and expandable frame without extending radially beyond the outermost surface of the outer periphery.

2. The prosthetic valve assembly of claim 1 wherein the outer periphery of the collapsible and expandable frame is substantially circular in cross section.

3. The prosthetic valve assembly of claim 1 wherein the sutures are threads, strands, fibers, or wires.

4. The prosthetic valve assembly of claim 1 wherein the plurality of recesses are rounded depressions.

5. The prosthetic valve assembly of claim 1 wherein the plurality of recesses are angular or polygonal depressions.

6. The prosthetic valve assembly of claim 1 wherein the plurality of recesses follow a perimeter of a cross-section of the plurality of spaced struts and nodes that connect the plurality of spaced struts.

7. The prosthetic valve assembly of claim 1 wherein a cross-section of the plurality of spaced struts is circular with a diameter that varies from the first end to the second end.

8. The prosthetic valve assembly of claim 1 wherein the plurality of spaced struts comprise wires, and wherein a diameter of the plurality of spaced struts varies from the first end to the second end.

9. The prosthetic valve assembly of claim 1 wherein the plurality of recesses are evenly spaced along each strut of the plurality of spaced struts.

10. The prosthetic valve assembly of claim 1 wherein at least one suture passes through at least one hole through the strut of the plurality of spaced struts.

11. The prosthetic valve assembly of claim 1 wherein the plurality of spaced struts are hollow.

12. The prosthetic valve assembly of claim 1 wherein the plurality of spaced struts are rectangular in cross section.

13. The prosthetic valve assembly of claim 1 wherein the plurality of spaced struts are rounded in cross section.

14. The prosthetic valve assembly of claim 1 wherein the plurality of spaced struts are polygonal in cross section.

15. An implantable prosthetic valve assembly comprising: a collapsible and expandable frame assembly having a plurality of vertical struts that define an outer periphery of the collapsible and expandable frame having an outermost surface; and a leaflet structure comprising a plurality of leaflets attached to the plurality of vertical struts by sutures, wherein the plurality of vertical struts include a plurality of holes that extend through the plurality of vertical struts, wherein the plurality of vertical struts include a plurality of recesses that extend radially inward from the outermost surface of the outer periphery; wherein the sutures are disposed in the plurality of recesses and extend through the plurality of holes, wherein the sutures secure the leaflet structure to the plurality of vertical struts without extending radially beyond the outermost surface of the outer periphery.

16. The prosthetic valve assembly of claim 15 wherein the outer periphery of the collapsible and expandable frame is substantially circular in cross section.

17. The prosthetic valve assembly of claim 15 wherein the sutures are threads, strands, fibers, or wires.

18. The prosthetic valve assembly of claims 15 wherein at least one of the vertical struts of the plurality of vertical struts includes at least one hole that passes from one side of the at least one vertical strut of the plurality of vertical struts to another side.

19. The prosthetic valve assembly of claim 15 wherein the plurality of vertical struts are hollow.

20. A prosthetic heart valve and catheter assembly comprising: a collapsible and expandable frame assembly having a plurality of spaced struts that extend from a first end of the collapsible and expandable frame to a second end of the collapsible and expandable frame and define an outer periphery of the collapsible and expandable frame having an outermost surface; wherein the plurality of spaced struts include a plurality of recesses that extend radially inward from the outermost surface of the outer periphery; and a prosthetic valve secured within the collapsible and expandable frame by sutures, wherein the sutures are disposed in the plurality of recesses; wherein the prosthetic heart valve and collapsible and expandable frame assembly are disposed and compressed inside a catheter, wherein the sutures secure the valve to the collapsible and expandable frame without extending radially beyond the outermost surface of the outer periphery.

21. The prosthetic valve and frame assembly of claim 20 wherein the outermost surface of the periphery contacts the catheter and further wherein the sutures are spaced apart from the catheter.

* * * * *